United States Patent
Detweiler et al.

(10) Patent No.: US 11,490,937 B2
(45) Date of Patent: Nov. 8, 2022

(54) BONE CLOSURE ASSEMBLY

(71) Applicant: Jace Medical, LLC, Warsaw, IN (US)

(72) Inventors: Jason F. Detweiler, Warsaw, IN (US);
Scott Steffensmeier, Roanoke, IN (US)

(73) Assignee: Jace Medical, LLC, Warsaw, IN (US)

( * ) Notice: Subject to any disclaimer, the term of this patent is extended or adjusted under 35 U.S.C. 154(b) by 0 days.

(21) Appl. No.: 17/117,545

(22) Filed: Dec. 10, 2020

(65) Prior Publication Data
US 2021/0177476 A1    Jun. 17, 2021

Related U.S. Application Data

(60) Provisional application No. 62/947,564, filed on Dec. 13, 2019.

(51) Int. Cl.
*A61B 17/82* (2006.01)
*A61B 17/88* (2006.01)
*A61B 17/00* (2006.01)

(52) U.S. Cl.
CPC ........ *A61B 17/823* (2013.01); *A61B 17/8861* (2013.01); *A61B 2017/00407* (2013.01)

(58) Field of Classification Search
CPC ......... A61B 17/82; A61B 7/823; A61B 7/842; A61B 17/8076; A61B 7/8861
See application file for complete search history.

(56) References Cited

U.S. PATENT DOCUMENTS

| | | | |
|---|---|---|---|
| 5,190,545 A | 3/1993 | Corsi et al. | |
| 5,339,870 A * | 8/1994 | Green | A61B 17/823 606/139 |
| 5,355,913 A * | 10/1994 | Green | A61B 17/823 140/123.6 |
| 6,007,538 A | 12/1999 | Levin | |
| 7,588,576 B2 | 9/2009 | Teague et al. | |
| 8,414,594 B2 | 4/2013 | Berger et al. | |
| 9,334,091 B2 * | 5/2016 | Zantout | B65D 63/00 |
| 10,307,193 B2 | 6/2019 | Garcia et al. | |
| 10,758,290 B2 | 9/2020 | Detweiler et al. | |
| 2005/0065521 A1 * | 3/2005 | Steger | A61B 17/80 606/291 |
| 2005/0192581 A1 * | 9/2005 | Molz | D04C 1/12 606/74 |
| 2009/0270923 A1 * | 10/2009 | Tormala | A61B 17/823 606/151 |
| 2010/0274249 A1 | 10/2010 | Dell'Oca | |
| 2012/0197256 A1 * | 8/2012 | Knueppel | A61B 17/8872 606/74 |
| 2013/0116736 A1 * | 5/2013 | De Oliveira | A61B 17/8861 606/86 R |
| 2016/0317161 A1 * | 11/2016 | Garcia | A61B 17/0482 |

(Continued)

FOREIGN PATENT DOCUMENTS

JP    3106821 U    11/2004

*Primary Examiner* — Matthew J Lawson

(74) *Attorney, Agent, or Firm* — Schwegman Lundberg & Woessner, P.A.

(57) ABSTRACT

A bone closure assembly that includes a buckle and a strap having a first end fixedly attached to the buckle. The strap is configured for looping around bone portions. The bone closure assembly also includes a locking cap removably connected to the buckle. The locking cap is configured for securing the strap within the buckle to secure the bone portions together.

19 Claims, 17 Drawing Sheets

(56) References Cited

U.S. PATENT DOCUMENTS

2018/0014865 A1* 1/2018 Golden ................ A61F 2/0811
2018/0177510 A1 6/2018 Whitaker et al.
2020/0367950 A1* 11/2020 Detweiler ............ A61B 17/846
2021/0100598 A1* 4/2021 Ensign ............... A61B 17/8869

* cited by examiner

BONE CLOSURE ASSEMBLY

CROSS REFERENCE TO RELATED APPLICATIONS

This is a non-provisional application based upon U.S. provisional patent application Ser. No. 62/947,564, entitled "BONE CLOSURE ASSEMBLY", filed Dec. 13, 2019, which is incorporated herein by reference.

BACKGROUND OF THE INVENTION

1. Field of the Invention

The present invention relates generally to bone closure devices for securing bone portions together, and more particularly, to a strap device and a handheld device for securing the strap device.

2. Description of the Related Art

Some surgical procedures involve separating a bone into portions and reuniting the bone portions after conducting the desired operation within the body. Various devices are used to refix or resecure the bone portions to one another. For example, in a sternal reapproximation medical procedure, one or more sternal fixation or closure devices can be used to hold and secure the portions of the sternum together. Generally, each sternal fixation device will engage or otherwise wrap around the sternal portions in order to hold and secure the sternal portions together.

One typical bone fixation device is a stainless-steel wire. In operation, the wire is wrapped around the bone portions to form a loop that engages with both of the bone portions. Thereafter, the ends of the wire are twisted around one another to tighten the loop and secure the bone portions together. Such wire-type fixation devices are cost-effective. However, these wire-type fixation devices may damage the bone portions by digging or cutting into the bone portions. Also, given the twist-tie nature of the wires, these wire-type sternal fixation devices may insufficiently or unevenly compress the bone portions together, which may undesirably result in movement, e.g. rubbing, of the bone portions and/or surrounding tissue.

Another typical bone fixation device is a bone plate. The bone plate has one or more threaded holes for receiving bone screws therein. The bone plate spans across the bone portions, and upon screwing the bone screws into the bone portions, the bone plate holds the bone portions together. However, it may be cumbersome and time-consuming to position and affix a bone plate onto bone portions.

What is needed in the art is an easy-to-use fixation device for efficiently securing bone portions.

SUMMARY OF THE INVENTION

The present invention provides a bone closure assembly that includes a strap device, a holder, and a handheld closing device. The strap device may include a buckle, a strap affixed to the buckle, and a locking cap removably connected to the buckle. The holder may hold the strap device. The holder may be removably connected to the handheld closing device.

The present invention in one form is directed to a bone closure assembly that includes a buckle and a strap having a first end fixedly attached to the buckle. The strap is configured for looping around bone portions. The bone closure assembly also includes a locking cap removably connected to the buckle. The locking cap is configured for securing the strap within the buckle to secure the bone portions together.

The present invention in another form is directed to a bone closure assembly that includes a holder configured for holding a bone closure device and a handheld closing device configured for receiving the holder and securing the bone closure device. The handheld closing device includes a first housing having an end configured for removably mounting the holder and a plunger rod disposed within the first housing. The plunger rod is configured for securing the securing member. The handheld closing device also includes a second housing connected to the first housing. The second housing includes a through-bore which is configured for receiving a strap therethrough upon the strap being looped around bone portions. The handheld closing device further includes a tightening member rotatably connected to the second housing. The tightening member is configured for tightening the strap.

The present invention in another form is directed to a method for securing bone portions. The method includes an initial step of providing a bone closure device to secure the bone portions, which includes a strap and a securing member, a holder configured for holding the bone closure device, and a handheld closing device configured for receiving the holder and securing the bone closure device. The handheld closing device includes a first housing having an end configured for removably mounting the holder, and a plunger rod disposed within the first housing. The plunger rod is configured for securing the securing member. The handheld closing device also includes a second housing connected to the first housing. The second housing includes a through-bore which is configured for receiving a strap therethrough upon the strap being looped around bone portions. The handheld closing device also includes a tightening member rotatably connected to the second housing. The method further includes inserting the holder into the end of the first housing, looping the strap around the bone portions, threading the strap through the securing member, and threading the strap through the through-bore of the second housing. The method further includes tightening the strap by rotating the tightening member, and actuating the plunger rod to secure the securing member such that the strap which is looped around the bone portions is fixed relative to the securing member.

An advantage of the present invention is that the strap device may simultaneously affix itself to the bone portions and secure the bone portions together.

Another advantage of the present invention is that the handheld closing device may efficiently position and secure the strap device in order to secure the bone portions together.

BRIEF DESCRIPTION OF THE DRAWINGS

The above-mentioned and other features and advantages of this invention, and the manner of attaining them, will become more apparent and the invention will be better understood by reference to the following description of embodiments of the invention taken in conjunction with the accompanying drawings, wherein.

DETAILED DESCRIPTION OF THE INVENTION

Figure 1:
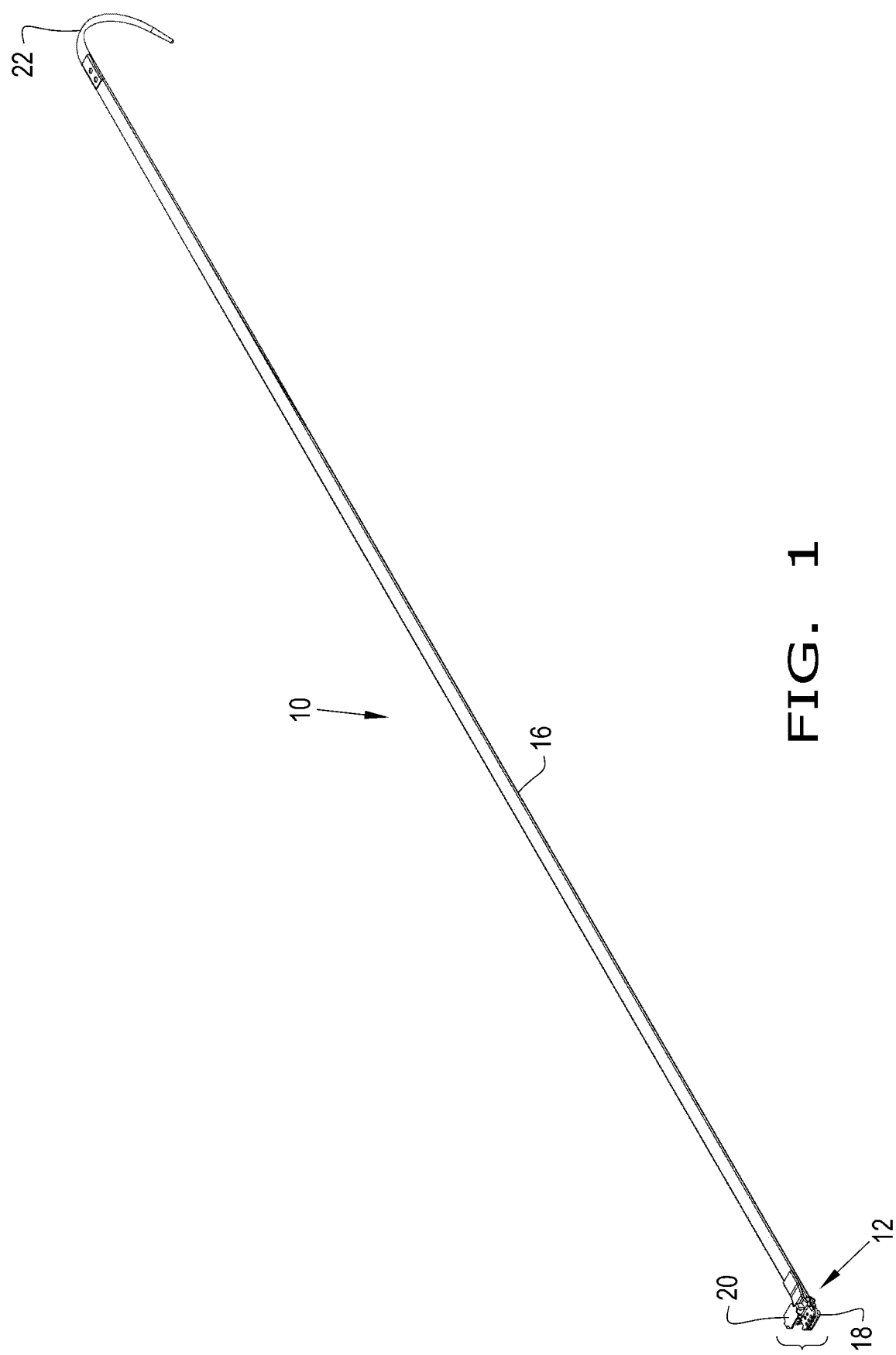
FIG. 1 is a perspective view of an embodiment of a bone closure assembly for wrapping around and securing bone portions, the bone closure assembly includes a strap device.

Referring now to the drawings, and more particularly to FIGS. 1-4, there is shown an embodiment of a bone closure assembly 10 that generally includes a strap device 12 and a holder 14, e.g. cage 14, for temporarily holding the strap device 12. The bone closure assembly 10 may be used to wrap around and secure a pair of separated bones, for example two halves of a sternum.

The strap device 12 may generally include a strap 16 and a securing member 18, 20 in the form of a buckle 18 and a removable locking cap 20. The strap device 12 may function as a cable-tie type device to loop around and retain bone portions. For instance, the strap device 12 may retain juxtaposed halves of a sternum without the aid of bone screws.

The strap 16 may be fixedly attached to the buckle 18. For example, one end of the strap 16, e.g. a fixed end, may be looped around a corresponding end of the buckle 18, and sewn back on itself or melted together. The opposite end of the strap 16, e.g. the free end, may be connected to a needle 22. For instance, the free end of the strap 16 may be sewn to a needle 22. In operation, the strap 16 may be looped around the halves of the sternum. The strap 16 may be in the form of any desired strap and may be composed of any desired material, such as a fibrous material, metal, and/or plastic. For example, the strap 16 may be a braided polymer. The strap 16 may have a uniform and rectangular cross-section. Also, the strap 16 may be in the form of a hollow tube that is collapsed on itself. However, the strap 16 may have any desired shape, including a varying contour with different widths. A small portion of the end of strap 16, may be stiffened. Furthermore, the width of the ends of the strap 16 may be necked down by way of a melting process.

Figure 2:
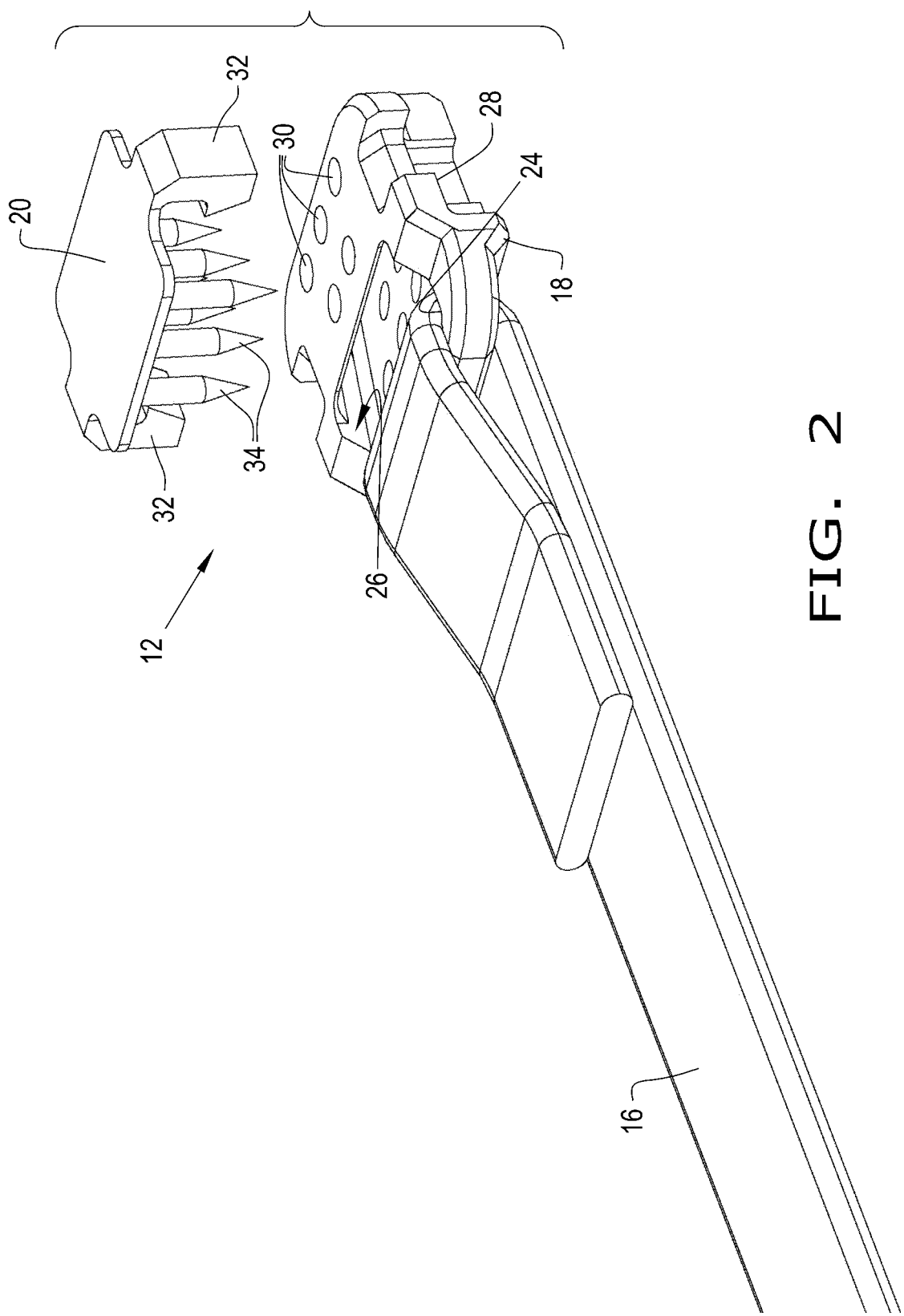
FIG. 2 is an exploded view of the strap device of FIG. 1.
Figure 3:
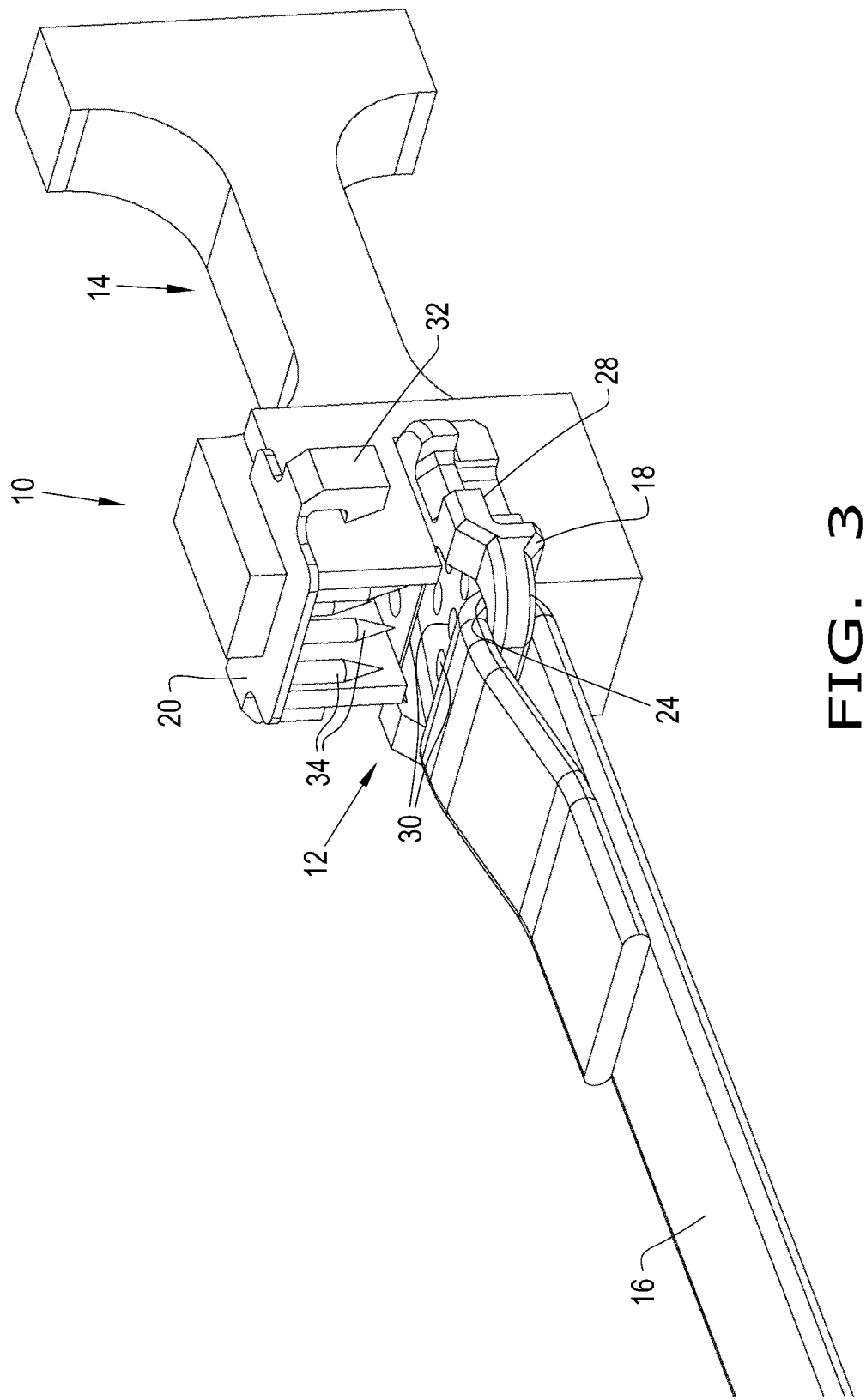
FIG. 3 is a perspective view of the bone closure assembly which includes the strap device and a holder for temporarily holding the strap device.

The buckle 18 may receive the strap 16 and the cap 20. The buckle 18 may include a body with slots 24, 26 for receiving the strap 16 (FIG. 2). One slot 24 may be a vertically disposed receiving slot 24 for receiving and fixedly mounting the looped and fixed end of the strap 16. The other slot 26 may be a horizontally disposed receiving slot 26 for receiving the free end of the strap 16. The buckle 18 may further include one or more mating features 28 and one or more through holes 30 for receiving the cap 20. For example, the buckle 18 may include a pair of mating features 28 and multiple through holes 30. Each mating feature 28 may be in the form of a two-tiered surface profile which defines a two-tiered groove. Each mating feature 28 may be located on a lateral side of the buckle 18. Each through hole 30 may extend through the entire body of the buckle 18. The buckle 18 may comprise any desired material, such as a metal and/or plastic material.

The cap 20 is configured for fixedly attaching to the buckle 18 and securing the strap 16 within the buckle 18. The cap 20 generally includes one or more arms or hooks 32 and one or more spikes 34. For example, the cap 20 may include two arms 32 and multiple spikes 34. The arms 32 and spikes 34 correspond to the mating features 28 and through holes 30 in the buckle 18, respectively. As the cap 20 is coupled to the buckle 18, the arms 32 will engage with the mating features 28 of the buckle 18. Also, the spikes 34 will pierce the strap 16 and retain the strap 16 within the buckle 18, thus preventing the strap 16 from loosening. The cap 20 may comprise any desired material, such as a metal and/or plastic material. The cap 20 may or may not be composed of the same material as the buckle 18.

Figure 4:
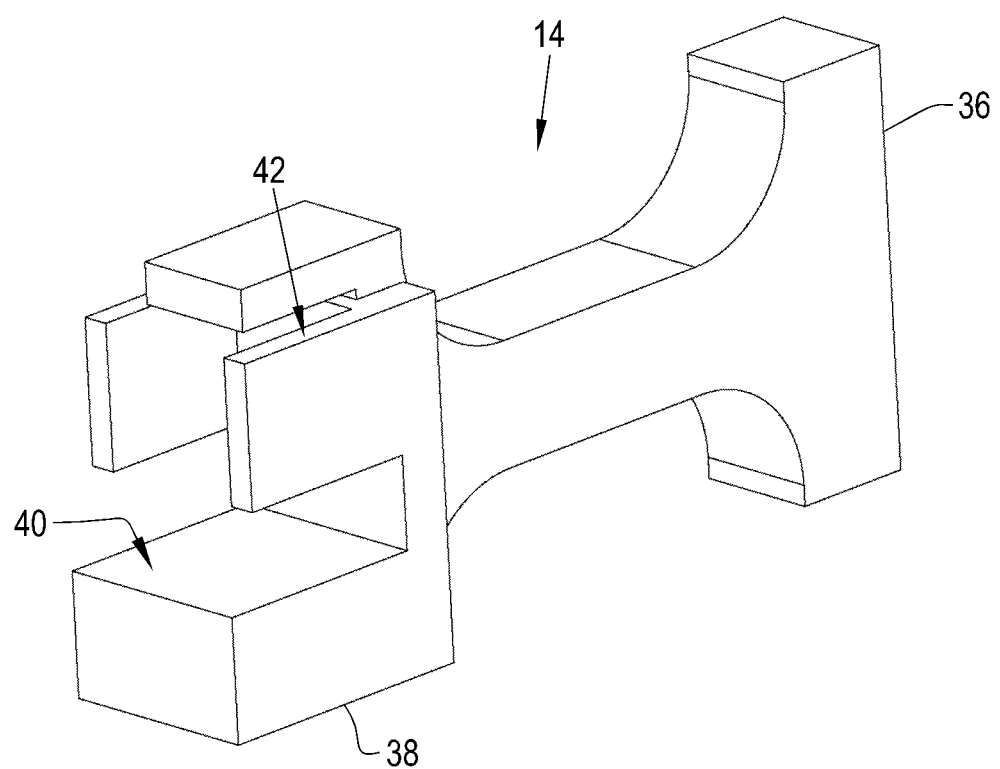
FIG. 4 is a perspective view of the holder of FIG. 3.

The cage 14 temporarily holds the buckle 18 and cap 20 together. The cage 14 generally includes a handle portion 36 and a mating portion 38 (FIG. 4). The handle portion 36 may be gripped by the user for easily positioning the strap device 12. The mating portion 38 may generally include a first, lower recess 40 for receiving at least a portion of the buckle 18 and a second, upper recess 42 for receiving at least a portion of the cap 20. Hence, the cage 14 may hold the cap 20 above the buckle 18 at a distance via the recesses 40, 42. It should be appreciated that the bone closure assembly 10 may be packaged in a particular configuration wherein the cage 14 supports both of the buckle 18 and the cap 20. Furthermore, the cage 14 may be used to rapidly load both the buckle 18 and the cap 20 into a positioning device, such as the tensioner 60 discussed herein. The cage 14 can then be removed and thrown away while leaving the cap 20 and the buckle 18 loaded in the tensioner 60.

Figure 5:
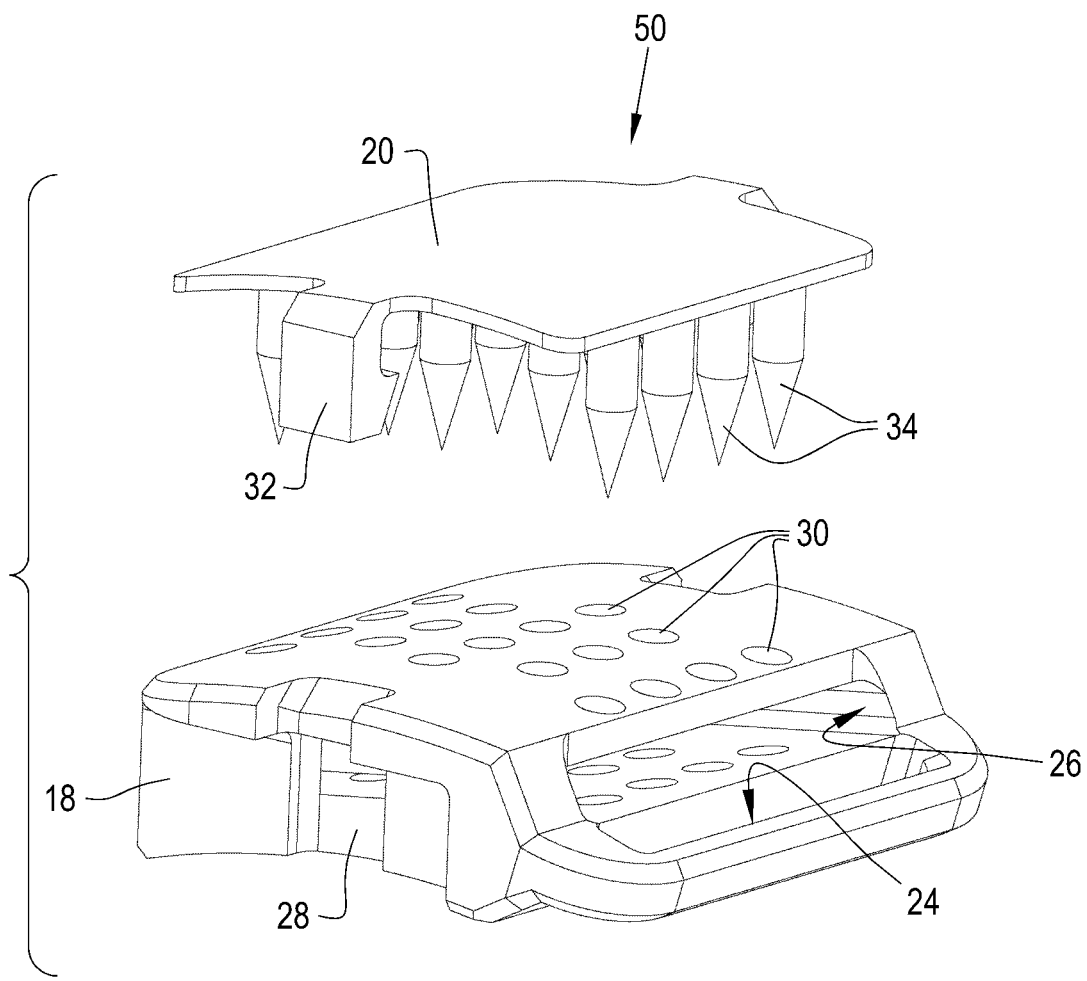
FIG. 5 is an exploded view of another embodiment of a bone closure assembly which includes a strap device.
Figure 6:
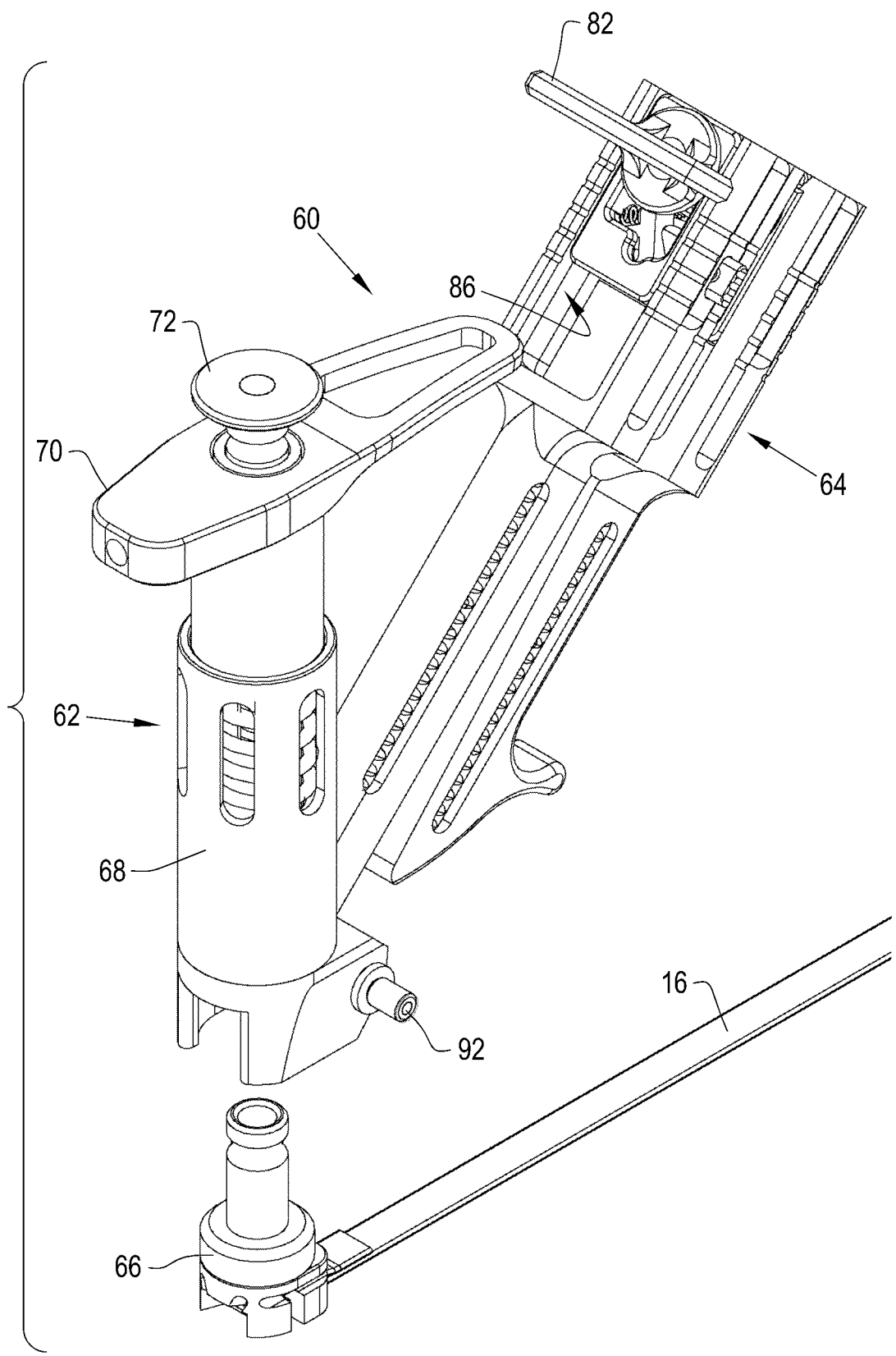
FIG. 6 is a perspective view of another embodiment of a bone closure assembly including a handheld closing device and a holder for holding a strap device, the holder is shown disconnected from the handheld closing device.
Figure 7:
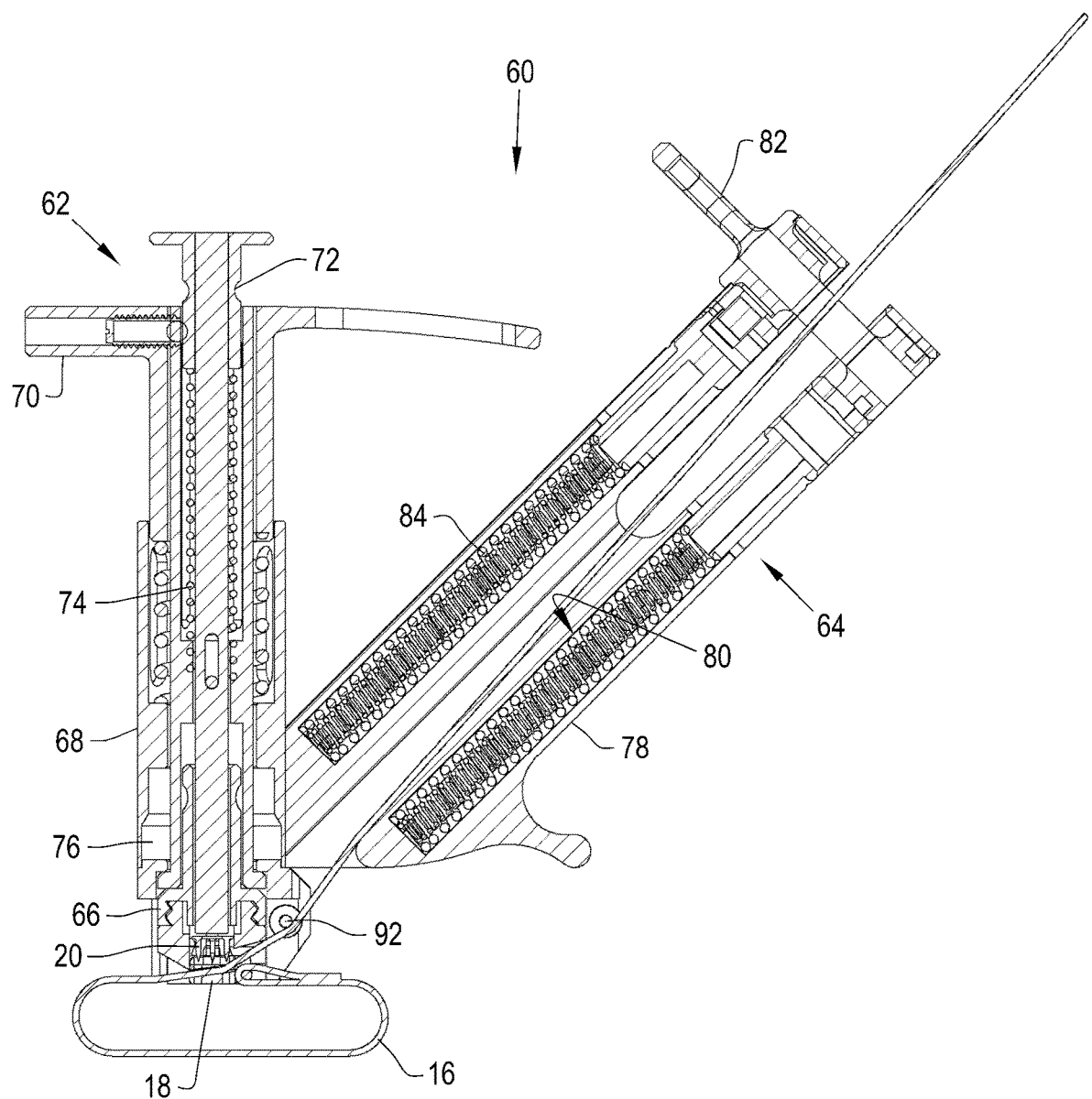
FIG. 7 is a cross-sectional view of the handheld closing device of FIG. 6, wherein the holder is positioned within the handheld closing device and the strap is wrapped through the buckle and the handheld closing device.
Figure 8:
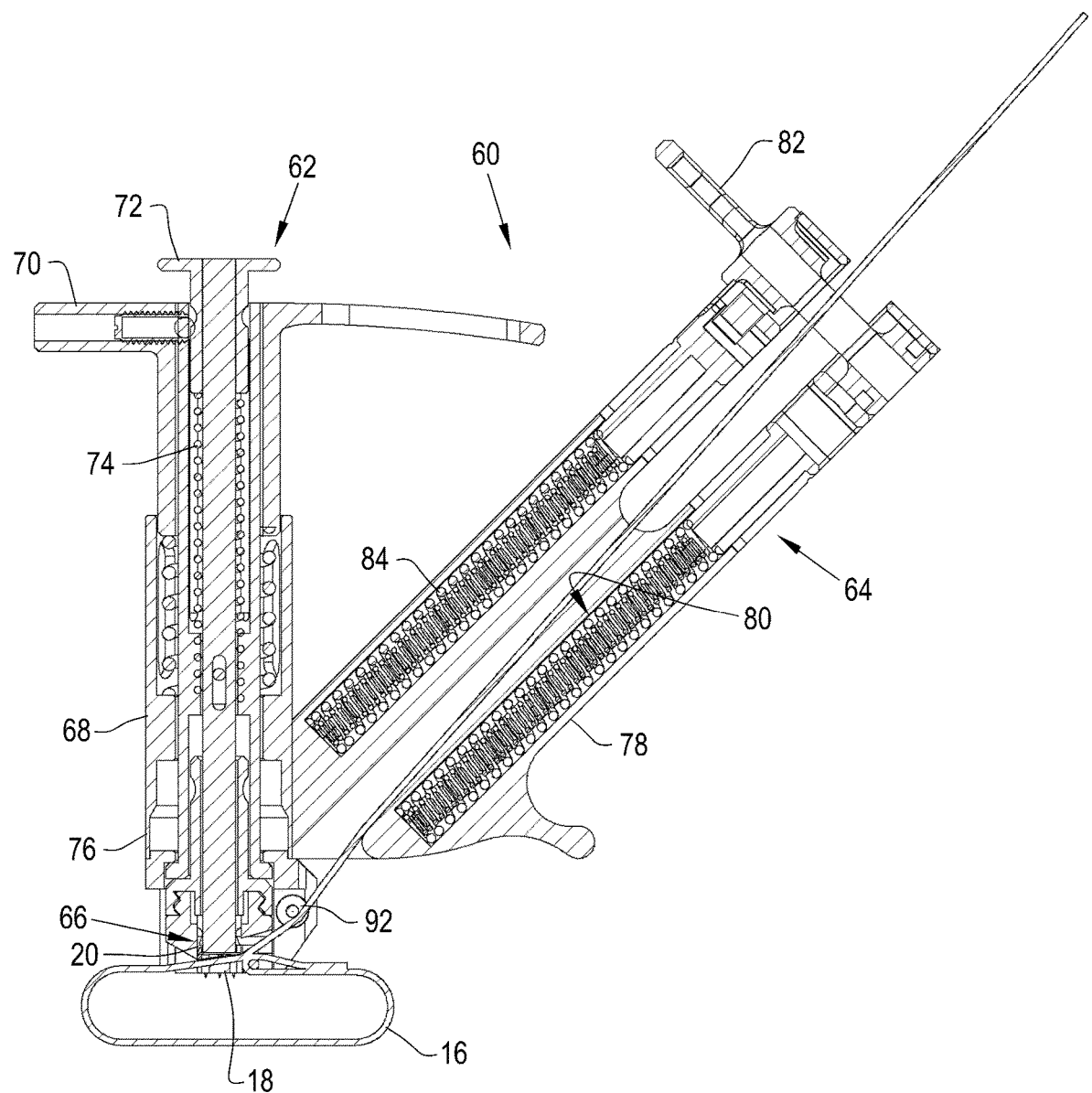
FIG. 8 is a cross-sectional view of the handheld closing device of FIG. 6, wherein the handheld closing device has deployed the cap onto the buckle to secure the strap around the bone portions.

Referring now to FIG. 5, there is shown another embodiment of a strap device 50. The strap device 50 may be substantially similar to the strap device 12, as discussed above, except that the strap device 50 is larger, includes a greater number of spikes 34, and has a curved contour. Thereby, the strap device 50 may conform to long bones, such as a femur. Like elements have been identified with like reference characters.

Referring now to FIGS. 6-9, there is shown another embodiment of a bone closure assembly which generally includes a handheld closing device 60 and a holder 66 for holding and securing a bone closure device, for example the strap device 12 as discussed above. The handheld closing device 60 is configured for collectively holding and positioning the strap device 12, tightening the strap 16, and engaging the cap 20 with the buckle 18 to secure the strap device 12. The handheld closing device 60 may be in the form of a tensioner 60. The tensioner 60 may generally include a plunger member 62 for deploying the cap 20, a tensioning member 64 for tensioning the strap 16, and a holder 66, e.g. cartridge 66, for holding the strap device 12. It should be appreciated that the tensioner 60 may be used to secure either strap device 12, 50, as discussed above. It should further be appreciated that the tensioner 60, including any component thereof, may be composed of any desired material, such as a metal and/or plastic material.

The plunger member 62 may generally include a housing 68, a handle 70, a plunger rod 72, one or more biasing members 74 for biasing the plunger rod 72, and a mating feature 76 for removably mounting the holder 66. The housing 68 may be a multipart housing that includes a lower portion and an upper portion that telescopes relative to the lower portion. The handle 70 allows the user to easily and firmly grip the plunger member 62. The plunger rod 72 is centrally disposed within the housing 68 and translates up and down relative to the housing 68. The plunger rod 72 at least partially extends into the holder 66 so that the distal end of the plunger rod 72 engages with and deploys the cap 20. The one or more biasing members 74 may be located within the housing 68. One biasing member 74 may be coaxially disposed around the plunger rod 72 and configured for upwardly biasing the plunger rod 72. Each biasing member 74 may be in the form of a coil spring. The mating feature 76 may be located within the housing 68, near the bottom end of the housing 68. The mating feature 76 may be in the form of a ball-detent type connector which allows the holder 66 to be removably coupled thereto.

The tensioning member 64 may be coupled to the plunger member 62 at an angle. The tensioning member 64 may be configured for tensioning the strap 16. The tensioning member 64 generally includes a housing 78 with a through-bore or cavity 80 therein for receiving the strap 16, a tightening or wrapping member 82 for winding the strap 16, and one or more biasing members 84 for biasing the wrapping member 82. The wrapping member 82 is rotatably and slidably mounted to the housing 78. The wrapping member 82 is mounted within designated tracks 86 in the housing 78. The wrapping member 82 has a receiving hole for allowing the strap 16 to be threaded therethrough. Once the strap 16 is threaded through the wrapping member 82, the wrapping member 82 may be twisted to shorten the looped strap 16 and temporarily hold the two halves of the sternum together. As tension is applied to the strap 16, the wrapping member 82 will slide down the tracks 86; and thus, an amount of tension may be indicated by the position of the wrapping member 82 relative to markings on the side of the housing 78. The wrapping member 82 may be in the form of a tensioning wheel such as an eye-bolt which acts as a one-way ratchet. Each biasing member 84 may be operably connected in between an end of the housing 78 and the wrapping member 82. Each biasing member 84 may be in the form of a coil spring.

Figure 9:
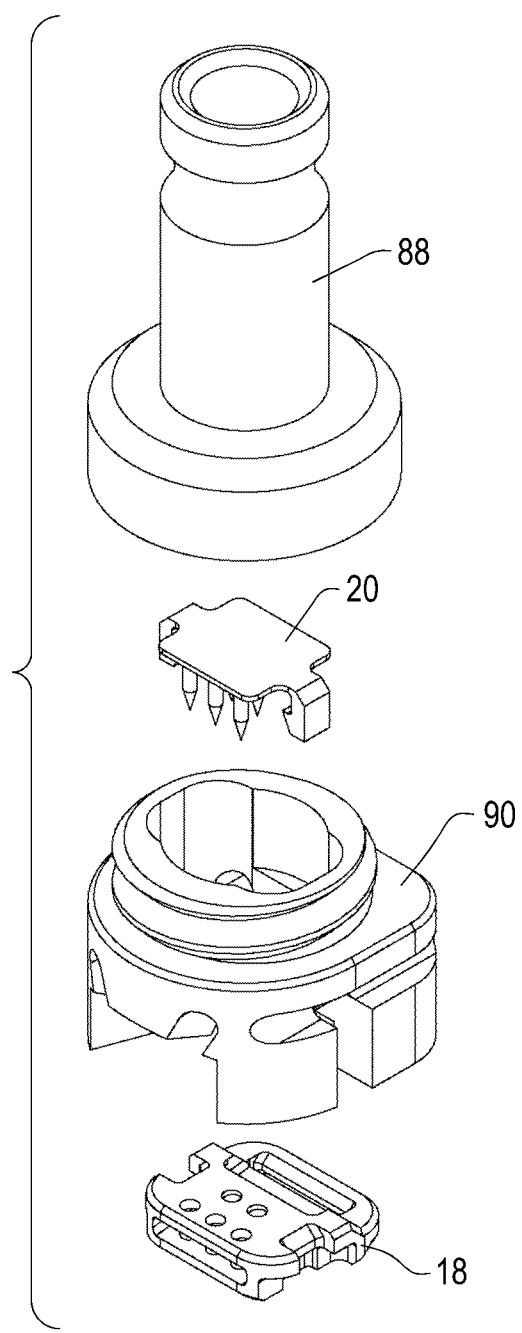
FIG. 9 is an exploded view of the holder and the strap device of FIGS. 6-8.
Figure 10:
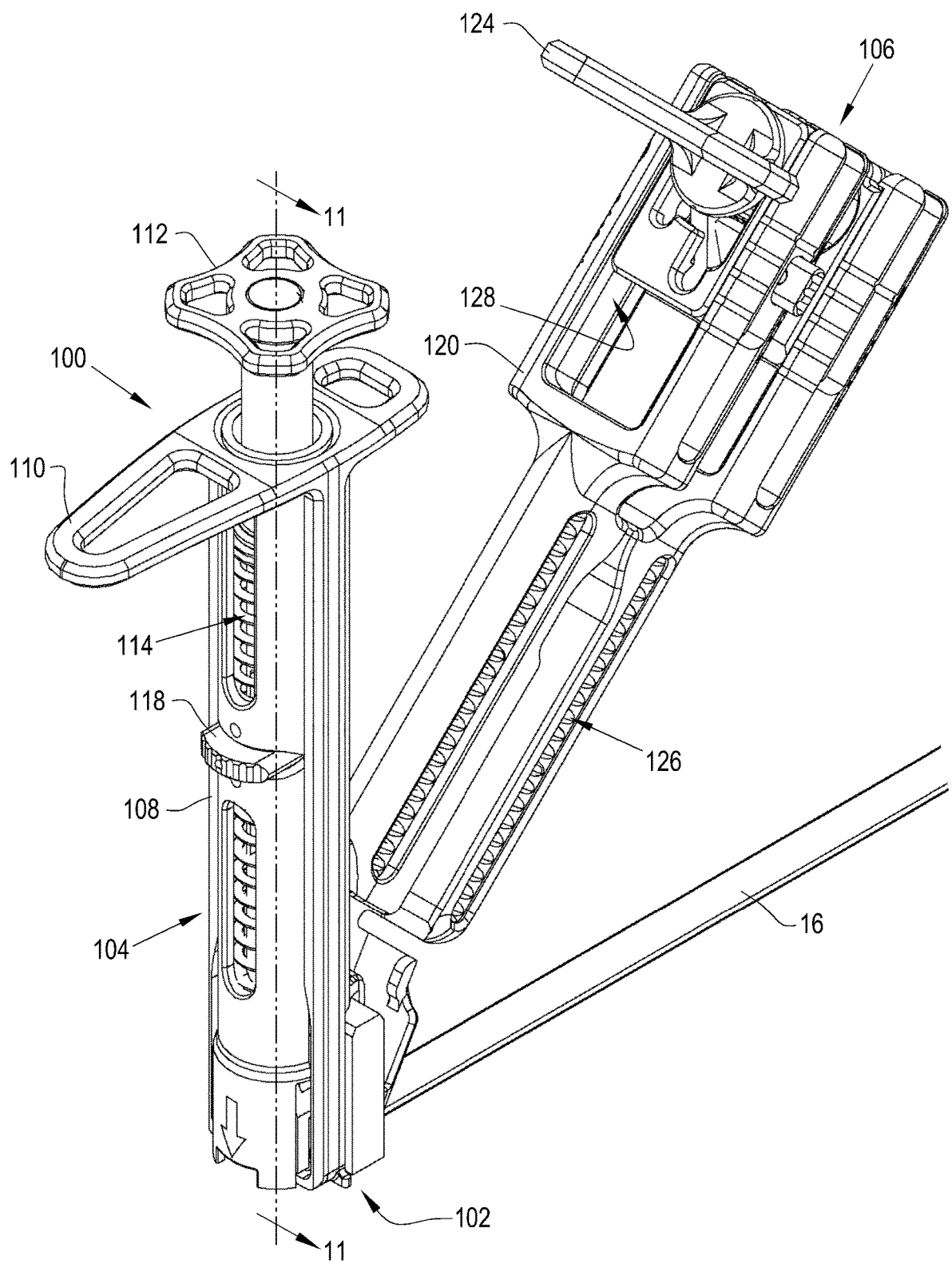
FIG. 10 is a perspective view of another embodiment of a bone closure assembly including a handheld closing device and a removable holder for holding a strap device, the holder is shown connected to the handheld closing device.
Figure 11:
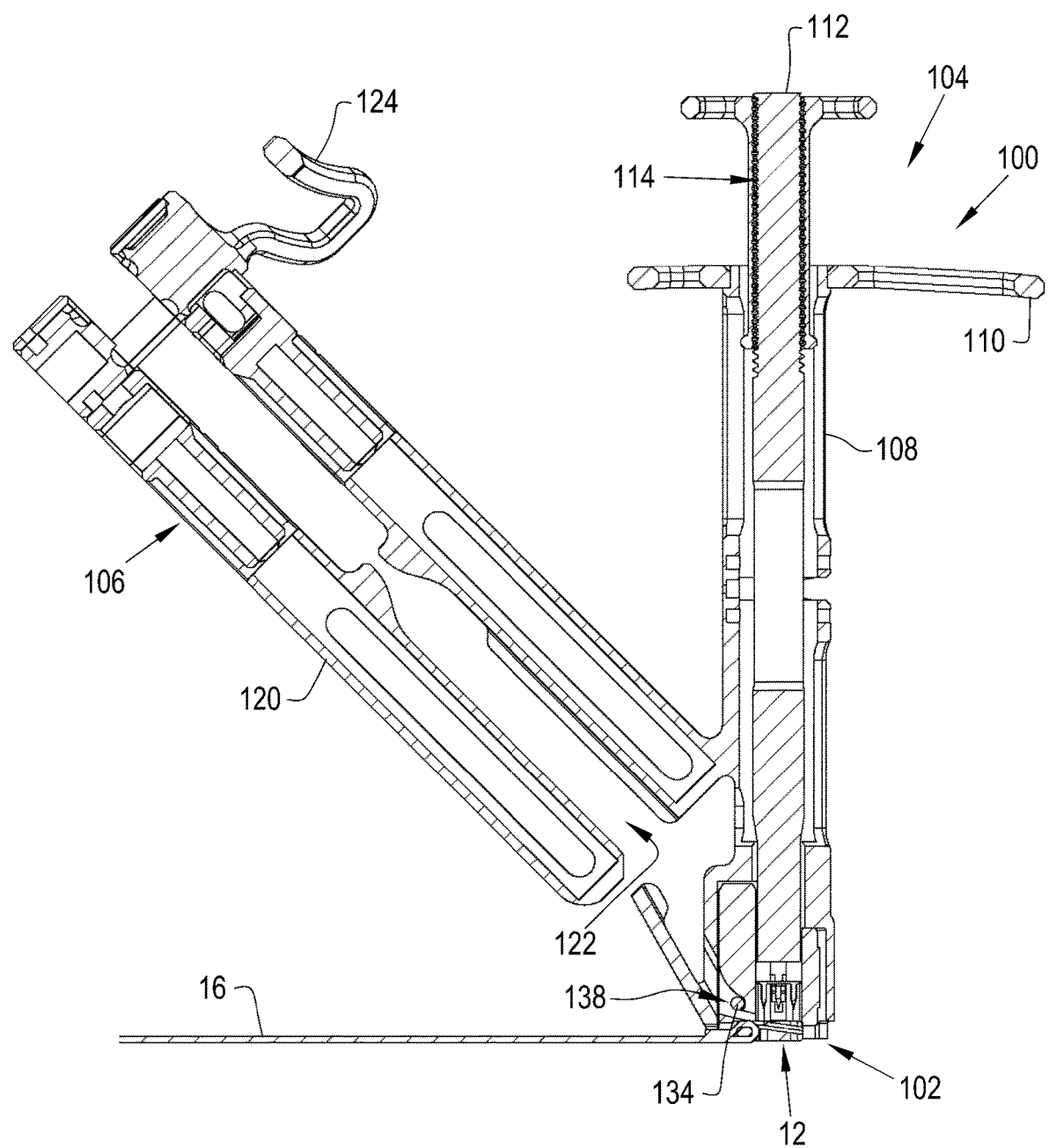
FIG. 11 is a cross-sectional view of the handheld closing device, taken across line 11-11 of FIG. 10.
Figure 12:
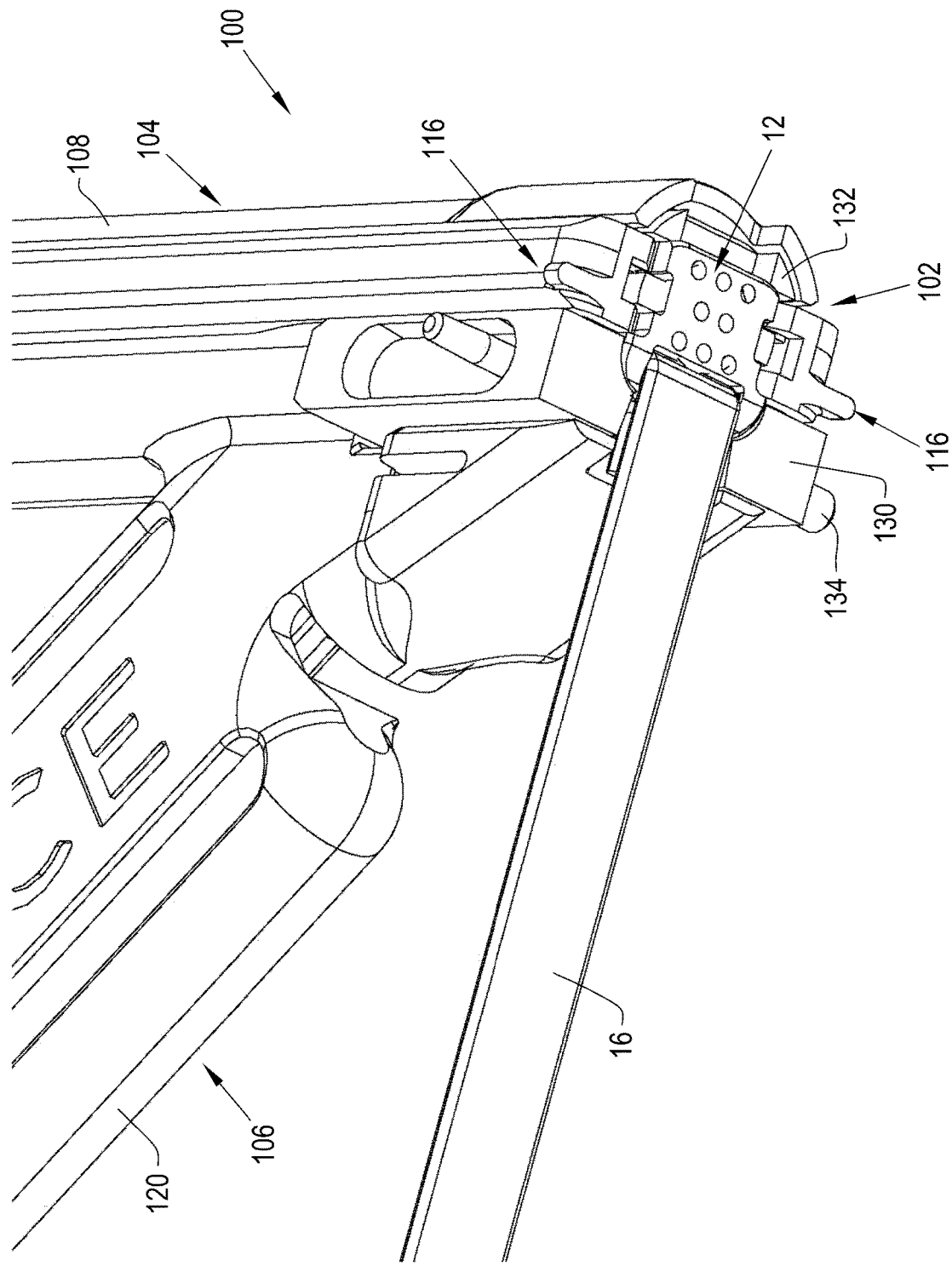
FIG. 12 is a perspective view of the end of the handheld closing device of FIGS. 10-11.
Figure 13:
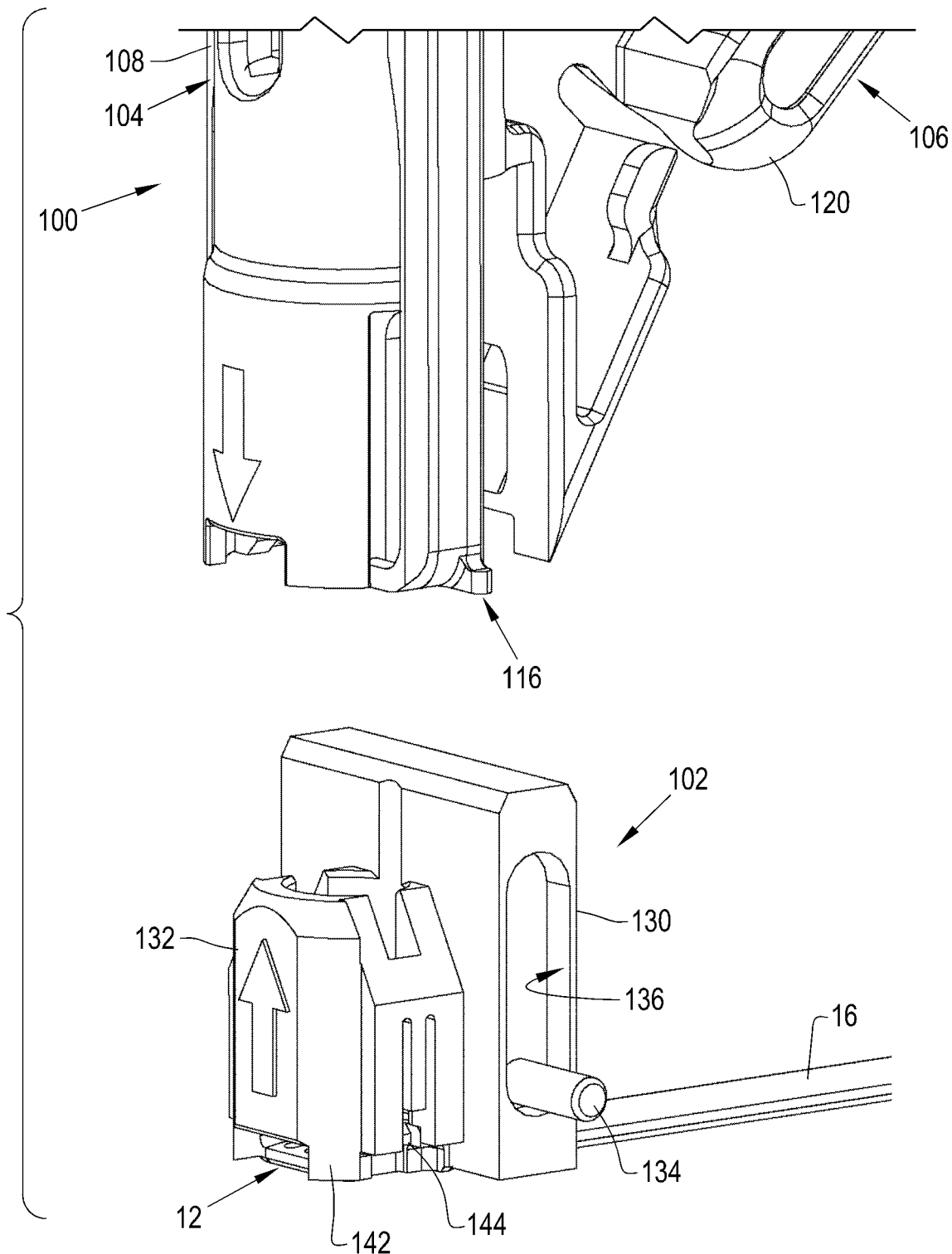
FIG. 13 is another perspective view of the end of the handheld closing device of FIGS. 10-11, wherein the holder is shown disconnected from the handheld closing device.
Figure 14:
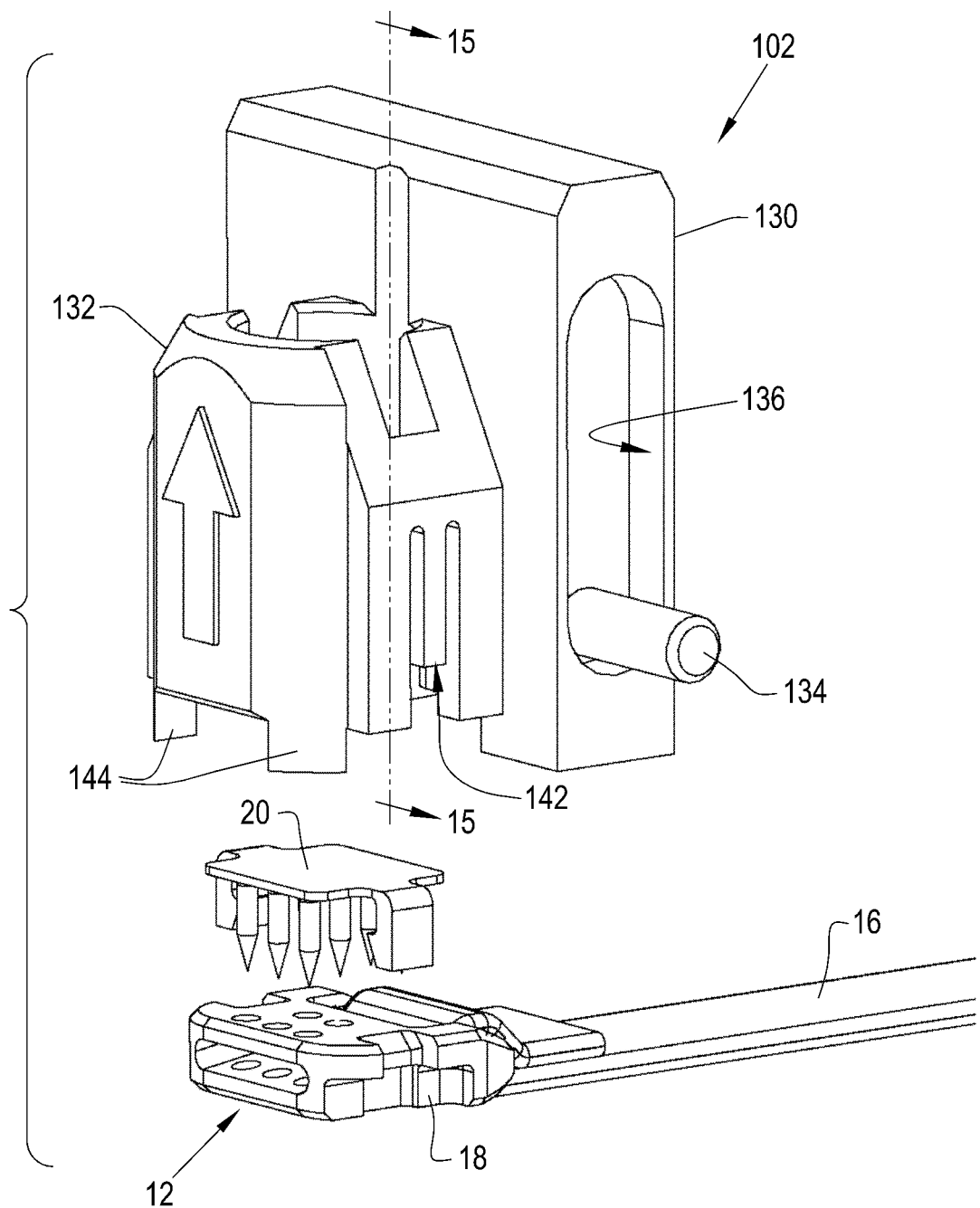
FIG. 14 is an exploded view of the holder and the strap device of FIGS. 10-13.

The holder 66 may be removably connected to the end of the plunger member 62. The holder 66 generally includes first and second holding members 88, 90 in the form of top and bottom connectors 88, 90 (FIG. 9). The holder 66, the buckle 18, and the cap 20 may be preassembled, packaged, and sterilized together. In operation, the user may open the sterilized package and remove the holder 66 with the buckle 18 and the cap 20 already preassembled therein.

The top connector 88 has a hollow stem portion and a threaded cylindrical portion which screws onto a corresponding threaded member of the bottom connector 90. The hollow stem portion of the top connector 88 engages with the mating feature 76 of the plunger member 62. The hollow stem portion of the top connector also has a through-bore which receives a portion of the plunger rod 72. The bottom connector 90 has an upper mounting portion, which is threaded, for dually receiving the cap 20 and the top connector 88. The bottom connector 90 also has a lower mounting portion for mounting the buckle 18 thereto. The holder 66 may comprise any desired material, such as a plastic material.

The tensioner 60 may also include a cautery bar 92 for cutting the strap 16 to a desired length. The cautery bar 92 may be integrated into the tensioner 60. For instance, the cautery bar 92 may be built into the plunger member 62. The cautery bar 92 may be located at the base of the plunger member 62. In this regard, the strap 16 may always be in contact with the cautery bar 92 once tension is applied to the strap 16. The cautery bar 92 is made of metal; however, the cautery bar 92 is surrounded by plastic which acts as an insulator. The user may contact the cautery bar 92 with a cauterizer, such as a Bovie® cautery, to transfer the electric current to the strap 16 which will result in the strap 16 being cut at the point of contact with the cautery bar 92.

In operation, the user forces the needle 22 of the strap device 12 through the soft tissue around the bones which are to be secured together. For example, the needle 22 may be forced through the soft tissue in the intercostal space on each side of the sternum. Thereafter, the needle 22 may be cut off and discarded. The stiffened and necked-down portion of the strap 16 is then fed through the buckle 18 in the tensioner 60 and subsequently through the wrapping member 82. Once the proper amount of tension has been applied, by twisting the wrapping member 82, the cap 20 can be coupled to the buckle 18 via actuating the plunger rod 72. For instance, a user may depress or downwardly push the plunger rod 72 so that the plunger rod 72 pushes the cap 20 onto the buckle 18. The arms 32 of the cap 20 mate with the mating features 28 in the buckle 18 and act as one-way barbs to prevent the cap 20 and the buckle 18 from uncoupling. Then, the excess strap 16 can be cut and/or cauterized via a cutter. For instance, the user may engage a cauterizer with the cautery bar 92 to dually seal and cut the strap 16, thus preventing fraying of the strap 16.

Referring now to FIGS. 10-15, there is shown an embodiment of a bone closure assembly which generally includes a handheld closing device 100 and a holder 102 for holding and securing a bone closure device, for example the strap device 12 as discussed above. The handheld closing device 100 may be configured for collectively holding and positioning the strap device 12, tightening the strap 16, and securing the strap device 12 by engaging the cap 20 with the buckle 18.

The handheld closing device 100 may generally include a plunger member 104 and a tensioning member 106. The plunger member 104 may receive the holder 102 and secure the strap device 12. The tensioning member 106 may receive and tension the strap 16. It should be appreciated that the handheld closing device 100 may be in the form of a tensioner 100. It should also be appreciated that the tensioner 100 may be used to secure either strap device 12, 50, as discussed above. It should further be appreciated that the tensioner 100, including any component thereof, may be composed of any desired material, such as a metal and/or plastic material.

The plunger member 104 may generally include a housing 108, a handle 110, a plunger rod 112, one or more biasing members 114 for biasing the plunger rod 112, and one or more mating feature 116 for removably mounting the holder 102. The plunger member 104 may also include a release button 118 for selectively engaging with and fixing the plunger rod 112 relative to the housing 108. Hence, the release button 118 may allow the user to deploy the plunger rod 112.

The housing 103 may have a through-bore or cavity for receiving the plunger rod 112 and the holder 102. The housing 108 may comprise the mating feature(s) 116 for removably mounting the holder 102. For example, the housing may have a pair of deformable arms 116 which grip onto the holder 102 such that the holder 102 may be snap fit within the housing 108. The housing 108 may be a monolithic or multipart housing.

The plunger rod 112 is centrally disposed within the housing 108 and translates up and down relative to the housing 108. The plunger rod 112 selectively moves into and out of the holder 102. For example, the plunger rod 112 may move downwardly into the holder to contact and engage the cap 20 with the buckle 18. Therein, the plunger rod 112 may push the cap 20 onto the buckle 18 and may further push the secured strap device 12 out of the holder 102. Additionally, the plunger rod 112 may move upwardly to disconnect the strap device 12 from the holder 102. The plunger rod 112 may have a contour and/or a mating feature which engages with and moves one or more portions of the holder 102 and/or the mating feature(s) 116 which retain the holder 102 within the housing 108. For example, upon moving upwardly, the plunger rod 112 may contact and push the mating features 116 outwardly and/or upwardly to cause the strap device 12 to drop out of the holder 102. Additionally or alternatively, for example, upon moving upwardly, the plunger rod 112 may contact and push the mating features 116 upwardly and/or outwardly to disengage the holder 102.

The one or more biasing members 114 may be located within the housing 108. Each biasing member 114 may be coaxially disposed around the plunger rod 112 and configured for upwardly biasing the plunger rod 112. Each biasing member 114 may be in the form of a coil spring.

The tensioning member 106 may be coupled to the plunger member 104 at an angle. The tensioning member 106 may be configured for receiving and tensioning the strap 16 after the strap 16 has been looped around bone portions. The tensioning member 106 generally includes a housing 120 with a through-bore or cavity 122 therein for receiving the strap 16, a tightening or wrapping member 124 for winding the strap 16, and one or more biasing members 126 for biasing the wrapping member 124.

The cavity 122 may guide the strap 16 into the wrapping member 124. The cavity 122 may also include one or more access ports, e.g. perpendicular recesses, for moving the strap 16 if needed. The cavity 122 may have any desired internal contour.

The wrapping member 124 is rotatably and slidably mounted to the housing 120. The wrapping member 124 is mounted within designated tracks 128 in the housing 120. The wrapping member 124 has a receiving hole for allowing the strap 16 to be threaded therethrough and accordingly wrapped therearound upon rotating the wrapping member 124. As tension is applied to the strap 16, the wrapping member 124 will slide down the tracks 128; and thus, an amount of tension may be indicated by the position of the wrapping member 124 relative to markings on the side of the housing 120. The wrapping member 124 may be in the form of a tensioning wheel such as an eye-bolt which acts as a one-way ratchet. The wrapping member 124 may also have one or more release buttons for selectively (un)locking a rotational movement and/or a translational movement relative to the housing 120 of the wrapping member 124.

Each biasing member 126 may be housed within a respective cavity or channel within the housing 120. Each biasing member 126 may be operably connected in between a lower end of the housing 120 and the wrapping member 124. Each biasing member 126 may be in the form of a coil spring.

The holder 102 may be removably connected to the end of the plunger member 104. The holder 102 may generally include a first member 130, a second member 132 fixedly attached to the first member 130, and an optional cautery bar 134. The first member 130 may be in the form of a block 130, such as a rectangular block 130, which mounts the second member 132. The first member 130 fits into a corresponding receiving hole at the end of the housing 108. The first member 130 may include a first slot 136 for receiving the cautery bar 134 and/or a cutting tool and a second slot 138, at its rear, for receiving the strap 16 and guiding the strap into the cavity 122 of the housing 120. The second member 132 may be in the form of a holding or mounting member which includes dually holds the cap 20 and the buckle 18. The second member 132 may include a through-bore 140, which also allows the plunger rod 112 to pass therethrough, upper retaining members 142 for holding onto the cap 20, and lower retaining members 144 for holding onto the buckle 18. The upper and lower retaining members 142, 144 may be in the form of downwardly extending arms or protrusions 142, 144. The cap 20 and the buckle 18 may be respectively snap-fit within the second member 132 via the upper and lower retaining members 142, 144. The upper retaining members 142 may have inwardly extending protrusions or hooks which wrap around and underneath the cap 20. As can be appreciated, the upper and lower retaining members 142, 144 may respectively define two recesses which correspond to the shape and size of the cap 20 and the buckle 18. It should be appreciated that the holder 102 and the strap device 12, or any desired member(s) of the strap device 12, may be preassembled, packaged, and sterilized together. The holder 102 may be a single use component such that it is discarded after use. The holder 102 may comprise any desired material, such as metal and/or plastic.

Figure 15:
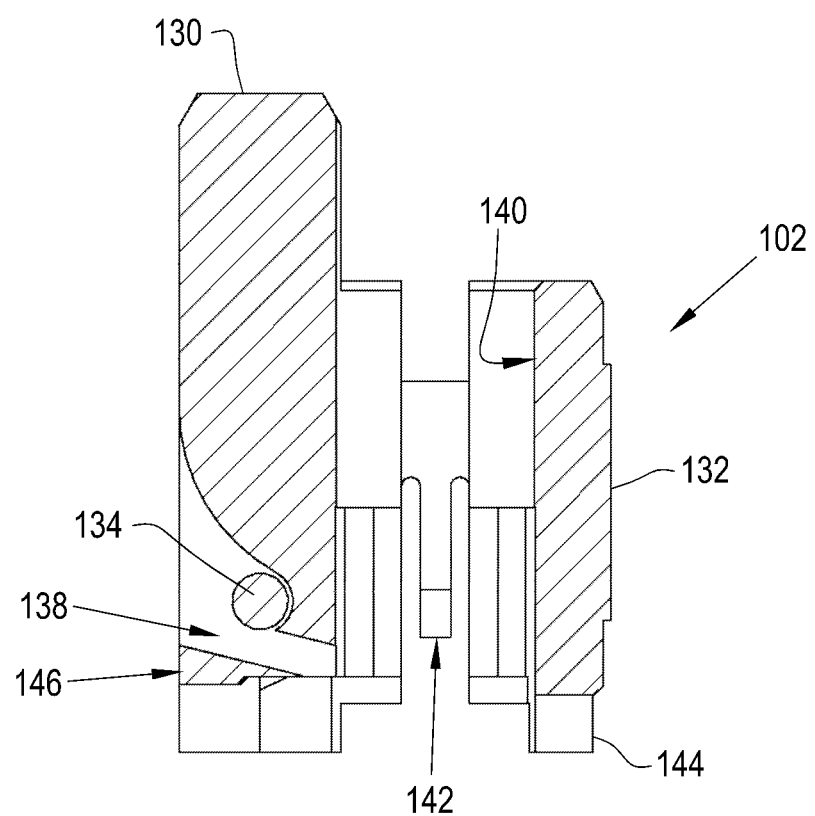
FIG. 15 is a cross-sectional view of the removable holder, taken across line 14-14 of FIG. 13.

The cautery bar 134 may integrated into the holder 102. The cautery bar 134 may be substantially similar to the cautery bar 92. Therein, a user may contact engage a cauterizer with the cautery bar 134 in order to cut and seal the strap 16. In order to protect other portions of the strap 16 from sparks and/or heat from the cauterizer, the holder 102 may include a blocking member 146 which extends across the second slot 138 (FIG. 15). The blocking member 146 may have a triangular cross-section. The blocking member 146 may comprise any desired material, such as metal and/or plastic. It should be appreciated that the slot 138 could be in the form of and/or include a metal insert to prevent a melting the holder 102.

Figure 16:
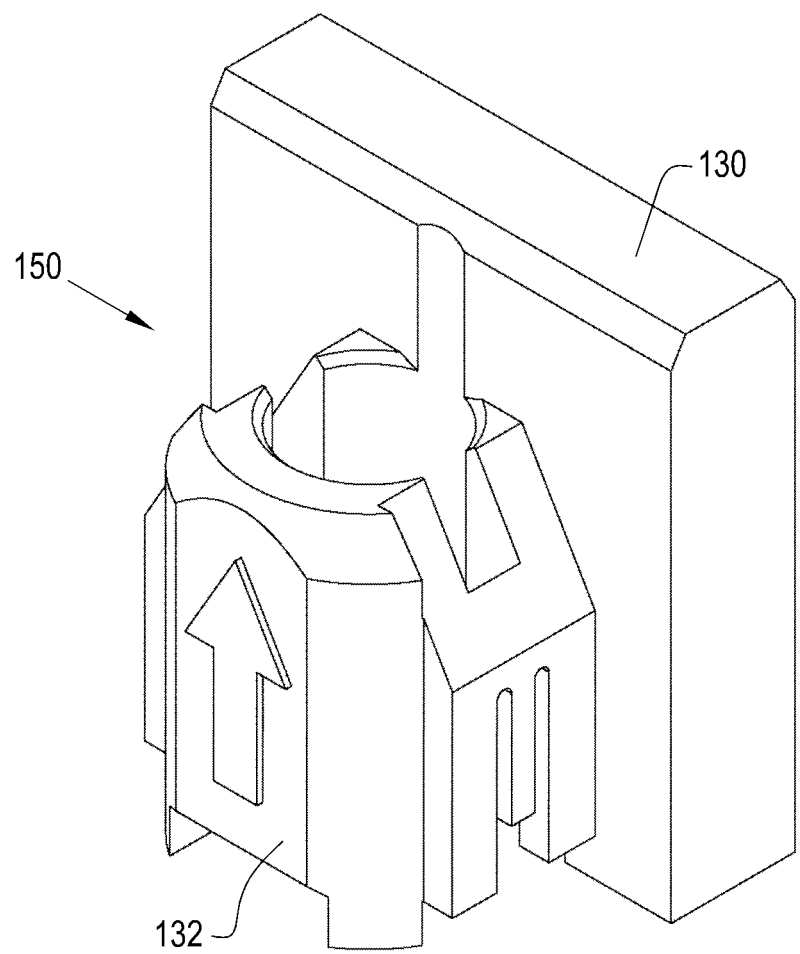
FIG. 16 is a perspective view of another embodiment of a removable holder, wherein the holder does not include a central slot.

Referring now to FIG. 16, there is shown another embodiment of a removable holder 150. The holder 150 may be substantially similar to the holder 102, as discussed above, except that the holder 150 does not include a cautery bar 134 or a slot 136 in the first member 130. Like elements have been identified with like reference characters.

Figure 17:
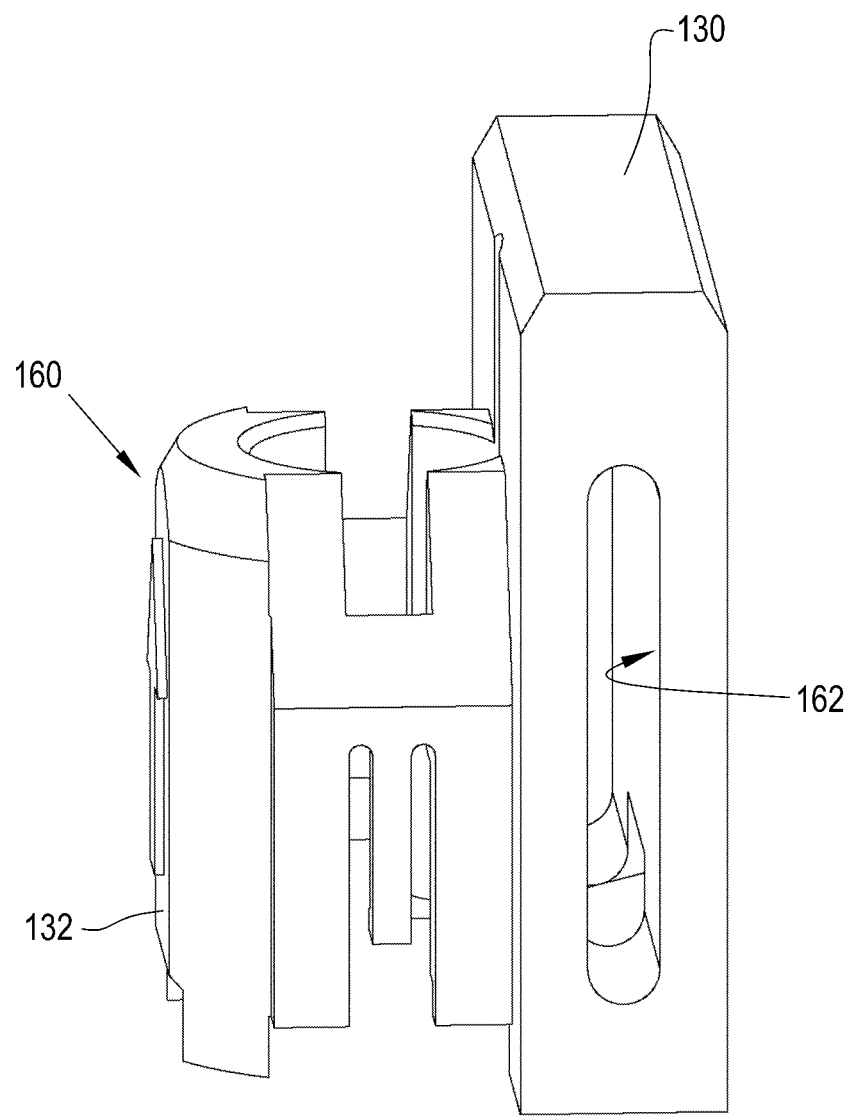
FIG. 17 is a perspective view of another embodiment of a removable holder, wherein the holder includes a central slot.

Referring now to FIG. 17, there is shown another embodiment of a removable holder 160. The holder 160 may be substantially similar to the holder 102, as discussed above, except that the holder 160 does not include a cautery bar 134. Additionally, the first member 130 of the holder 160 may include an enlarged slot 162 that extends through the body of the first member 130. The slot 162 may receive a cutting tool for cutting the strap 16. Like elements have been identified with like reference characters.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. A bone closure assembly, comprising:
a buckle;
a strap comprising a first end fixedly attached to the buckle, the strap being configured for looping around bone portions;
a locking cap removably connectable to the buckle, the locking cap being configured for securing the strap within the buckle to secure the bone portions together;
a handheld closing device comprising a first housing and a plunger rod that is translatable within the first housing; and
a holder received in a distal end of the first housing, the holder releasably holding the locking cap and the buckle,
wherein the holder comprises a distal portion and a proximal portion, the distal portion comprising an upper mounting portion in which the locking cap is removably received and a lower mounting portion in which the buckle is removably received, the proximal portion providing a plunger through-bore through which a distal end of the plunger rod can be moved in a distal direction toward the locking cap for forcibly engaging the locking cap in the holder to secure the locking cap to the buckle.

2. The bone closure assembly of claim 1, wherein the buckle comprises at least one mating feature configured for receiving the locking cap.

3. The bone closure assembly of claim 2, wherein the buck comprises a pair of mating features configured for receiving the locking cap.

4. The bone closure assembly of claim 3, wherein the locking cap comprises a pair of arms configured for respectively engaging with the pair of mating features of the buckle.

5. The bone closure assembly of claim 1, wherein the buckle comprises a first slot for mounting the first end of the strap and a second slot configured for receiving the strap upon the strap being looped around the bone portions.

6. The bone closure assembly of claim 1, wherein the buckle comprises a plurality of through holes.

7. The bone closure assembly of claim 6, wherein the locking cap comprises a plurality of spikes configured for respectively extending through the plurality of through holes of the buckle for piercing and retaining the strap within the buckle.

8. The bone closure assembly of claim 1, wherein the proximal portion of the holder and the distal portion of the holder are separately formed pieces removably connected to one another.

9. The bone closure assembly of claim 8, wherein the proximal portion of the holder comprises an elongate hollow stem portion through which the plunger through-bore extends.

10. The bone assembly of claim 1, wherein the strap comprises a second end, wherein the bone closure assembly further comprises a needle connected to the second end of the strap.

11. The bone closure assembly of claim 1, wherein the buckle and the locking cap each comprise a curved contour.

12. A bone closure assembly, comprising:
a holder releasably holding a locking cap and a buckle of a bone closure device; and
a handheld closing device configured for receiving the holder and operable to secure the locking cap to the buckle, the handheld closing device comprising:
a first housing comprising a distal end in which the holder is removably received, the first housing further comprising a longitudinal through-bore that is in communication with the distal end of the first housing;
a plunger rod disposed within the first housing so as to be translatable back and forth within the longitudinal through-bore, wherein, via translation of the plunger rod in the longitudinal through-bore, a distal end of the plunger rod can be moved in a distal direction through a proximal portion of the holder to forcibly engage the locking cap in the holder for securing the locking cap to the buckle;
a second housing connected to the first housing, the second housing comprising a strap through-bore which is configured for receiving a strap therethrough upon the strap being looped around bone portions; and
a tightening member rotatably connected to the second housing, the tightening member being configured for tightening the strap.

13. The bone closure assembly of claim 12, wherein the distal end of the first housing comprises a mating feature which is configured for removably mounting the holder.

14. The bone closure assembly of claim 13, wherein the mating feature is in the form of one of a ball-decent type connector and a receiving slot.

15. The bone closure assembly of claim 12, further comprising a cautery bar integrated into one of the holder and the handheld closing device, the cautery bar being configured for cutting the strap.

16. The bone closure assembly of claim 12, wherein the holder comprises a first holding member and a second holding member removably connected to the first holding member, the first holding member providing the proximal portion of the holder through which the distal end of the plunger rod can be moved to forcibly engage the locking cap.

17. The bone closure assembly of claim 16, wherein the second holding member comprises an upper mounting portion and a lower mounting portion, wherein the upper mounting portion is configured for receiving the locking cap of the bone closure device, wherein the lower mounting portion is configured for receiving the buckle of the bone closure device.

18. The bone closure assembly of claim 12, wherein the holder comprises upper retaining arms and lower retaining arms, wherein the upper and lower retaining arms are respectively configured for holding the locking cap and the buckle of the bone closure device.

19. The bone closure assembly of claim 12, wherein the tightening member is in the form of a one-way ratchet that is configured for receiving the strap and rotating to wrap the strap therearound.

\* \* \* \* \*